(12) United States Patent
Khiyami

(10) Patent No.: US 9,181,522 B2
(45) Date of Patent: Nov. 10, 2015

(54) METHOD AND APPARATUS FOR ASEPTIC TRANSFER OF BIOLOGICAL MATERIAL

(71) Applicant: Mohammad Ahmed Khiyami, Riyadh (SA)

(72) Inventor: Mohammad Ahmed Khiyami, Riyadh (SA)

(73) Assignee: King Abdulaziz City for Science and Technology (KACST), Riyadh (SA)

( * ) Notice: Subject to any disclaimer, the term of this patent is extended or adjusted under 35 U.S.C. 154(b) by 399 days.

(21) Appl. No.: 13/849,482

(22) Filed: Mar. 23, 2013

(65) Prior Publication Data

US 2014/0287482 A1   Sep. 25, 2014

(51) Int. Cl.
*B01L 3/02* (2006.01)
*C12M 1/12* (2006.01)
*C12M 1/30* (2006.01)
*G01N 35/10* (2006.01)
*C12M 1/26* (2006.01)

(52) U.S. Cl.
CPC ............... *C12M 37/00* (2013.01); *C12M 33/02* (2013.01); *A61L 2202/122* (2013.01); *A61L 2202/18* (2013.01); *B01L 3/0275* (2013.01); *B01L 3/0279* (2013.01); *C12M 1/26* (2013.01); *C12M 1/262* (2013.01); *C12M 1/265* (2013.01); *G01N 35/10* (2013.01); *G01N 2035/103* (2013.01)

(58) Field of Classification Search
CPC ............ G01N 2035/103; G01N 35/10; G01N 35/1004; G01N 35/1074; B01L 3/0275; B01L 3/0279; A61L 2202/122; A61L 2202/18; C12M 1/26; C12M 1/262; C12M 1/265
USPC .......................................................... 422/511
See application file for complete search history.

(56) References Cited

U.S. PATENT DOCUMENTS

| | | | |
|---|---|---|---|
| 6,474,888 B1* | 11/2002 | Lapstun et al. | 401/45 |
| 2005/0239200 A1* | 10/2005 | Beckwith et al. | 435/299.1 |
| 2009/0016801 A1* | 1/2009 | Liu | 401/116 |
| 2013/0017568 A1* | 1/2013 | Enriquez | 435/30 |

\* cited by examiner

*Primary Examiner* — Jill Warden
*Assistant Examiner* — Brittany Fisher
(74) *Attorney, Agent, or Firm* — Geeta Kadambi; Riddhi IP LLC

(57) ABSTRACT

The present application discloses a novel biological material transfer apparatus and methods of using the same. The apparatus is made up of double walled barrel shaped tip chamber to house either the single tip or multiple tips of fixed size and a unique ball head to transfer the biological material from one location to another location in an aseptic method. The tip has a fixed shape and size and a ball head which makes the process of picking and transferring of biological material easy, safe and convenient to use with large scale samples. The apparatus is further equipped with an ultra violet light which sterilize the tips just before their use making the entire process of transferring of biological material highly aseptic.

16 Claims, 6 Drawing Sheets

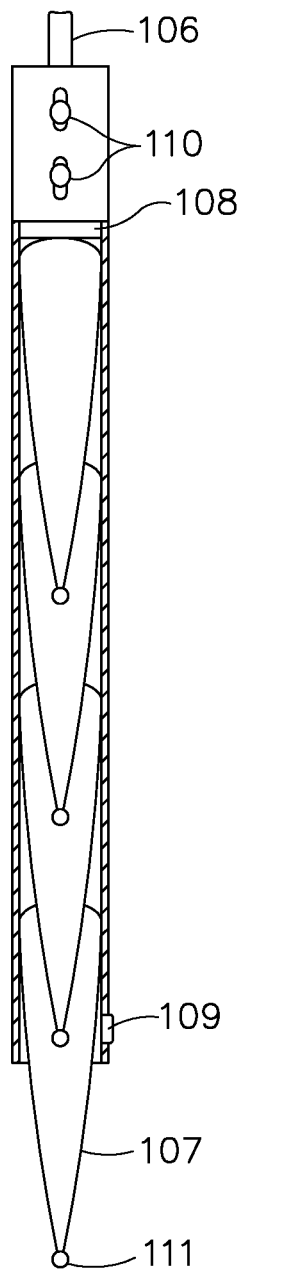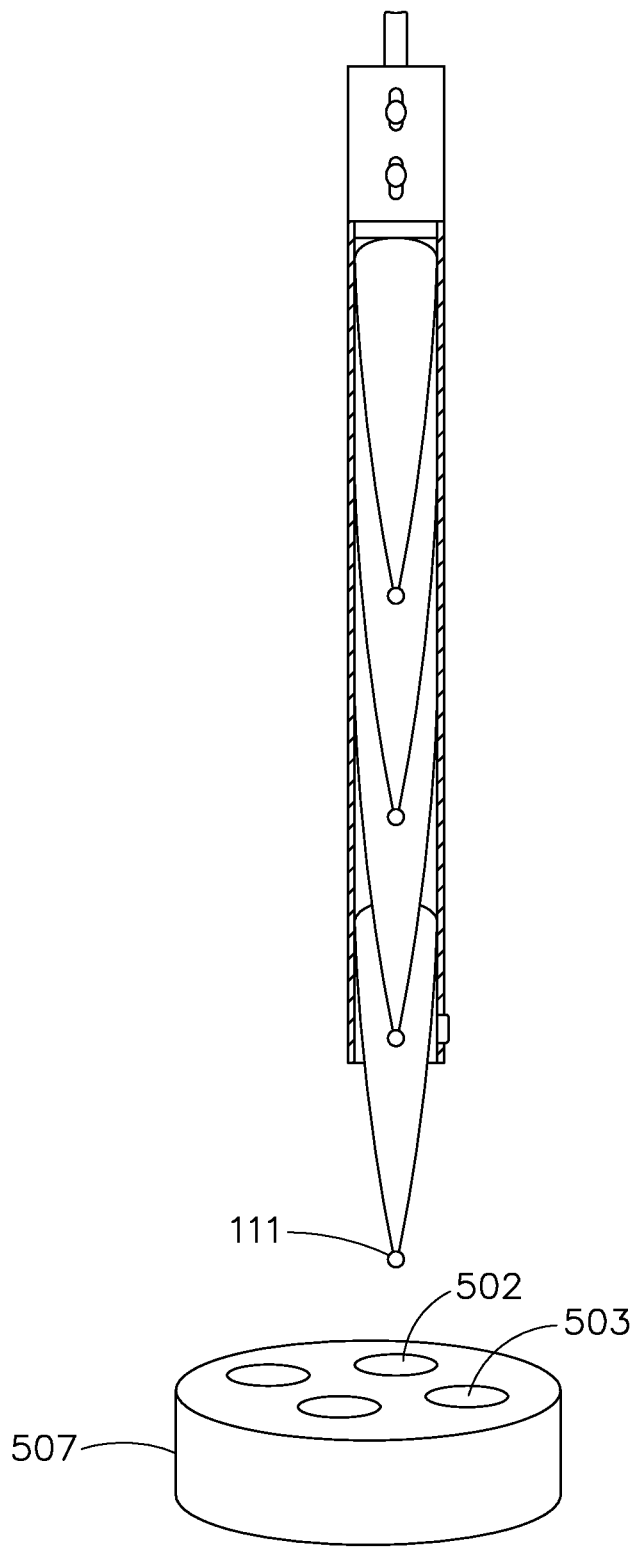
FIG.5A
FIG.5B

METHOD AND APPARATUS FOR ASEPTIC TRANSFER OF BIOLOGICAL MATERIAL

FIELD OF TECHNOLOGY

The present disclosure is related to an apparatus for picking and transferring the biological material in an aseptic manner and methods of using the same. More specifically, the present disclosure generally relates to an apparatus to pick and transfer bacteriological material from one location to another and methods of using the same.

BACKGROUND

An important aspect of bacteriological culturing and sub-culturing techniques is to keep contamination to minimum while transferring the bacterial colonies to ensure accurate results. For this, a number of culturing apparatus and culturing equipment's are in use till date to prevent and/or avoid contamination of the cultures and also to protect the users from exposure to harmful pathogens.

The aseptic procedure in use for culturing, sub-culturing and purifying bacteria include ways to transfer bacterial or other biological material from one culture media to another by using transfer tools while also maintaining highly aseptic conditions.

Tools most commonly and routinely used in microbiological laboratories include inoculating loops and needles (to transfer bacteria), bunsen burners and incinerators. Working under aseptic conditions includes sterilizing the inoculating loop or needle. This is a multi-step process and includes heating the inoculating loop in a flame until it becomes red hot, cooling the inoculating loop in alcohol before touching the culture, picking up the organism to be transferred, transferring the culture to a new container and heating the inoculating loop again to destroy any remaining organism. One of the biggest disadvantages of working under the procedure is sterilization of the entire process which has to be repeated with every single transfer of biological material. This makes the whole process cumbersome, unsuitable and unsafe as many a times needle is not sufficiently sterilized or the needle might get over heated which can kill the biological material. Also, the whole process can be hazardous for inexpert user or can be accidental if the alcohol and bunsen burner are not in a sufficiently safe distance.

Laboratories also use plastic disposable loops instead of metal loops/needles to transfer the biological material. These are pre-sterilized however still pose certain disadvantages as to the quantity and ease with which the loops can be used. For example, the box of the disposable loops has to be both handy and in a safe environment so that user can take out one loop at a time and have to be cautious in resealing the box/bag immediately to prevent contamination and thus is not convenient for processing large number of sample.

Thus, there is still a long-felt need for safe, easy to handle and time saving apparatus to transfer biological material and further to prevent its users from exposure to hazardous exposure to biological material.

SUMMARY

The following brief summary is not intended to include all features and aspects of the present invention, nor does it imply that the invention must include all features and aspects discussed in this summary.

Apparatus and methods of its use are provided to transfer biological material from one location to another location in an aseptic manner with ease in both small and large sample settings.

In one embodiment, the apparatus has a double-walled barrel shaped chamber or tip chamber comprising of an inner wall and an outer wall. A UV light source may be housed on the inner wall or the outer wall of the chamber. In another embodiment, the outer wall of the chamber may have an ON and OFF switch to operate the UV light source. The UV light source may be switched ON to sterilize the apparatus before use and also just before using the tip for transferring the biological material.

In one embodiment, the tip chamber has a score or push lid which can be opened and closed to load sterile disposable tips into the tip chamber. In another embodiment, one end of the tip chamber has a push eject button. The push eject button can be used to lower the sterile disposable tips into the tip chamber and also to discard the tips once the biological material transfer is complete.

The disposable tips are autoclavable with fixed size and ball head. The ball shaped head tip makes the apparatus easy to use and easy to pick up the biological material in any form for transfer. The disposable tips may be sterilized before and after loading into the tip chamber. The disposable tips can be loaded both for a single use and for multiple uses. The tips have a circumference of size that is less than the circumference of the inner wall of the tip chamber so that it can be fit and pass through the tip chamber smoothly during its use.

In some embodiments, the apparatus may consist of spring structure to dispense the disposable tips from the tip chamber.

In one embodiment, a method of using a sterile disposable tip to transfer the biological material from one location to another location in an aseptic way is disclosed. The biological material to be transferred may be on a flat petri dish, test tube, conical flask or other routinely used culture laboratory apparatus. In another embodiment, a method of loading the sterile disposable tips into the tip chamber by opening and closing the score lid is disclosed.

The novel apparatus and methods of using the apparatus, disclosed herein, may be implemented in any means for achieving various aspects. Other features will be apparent from the accompanying figures and from the detailed description that follows.

BRIEF DESCRIPTION OF THE DRAWINGS

Example embodiments are illustrated by way of example and no limitation in the tables and in the accompanying figures, like references indicate similar elements and in which.

Other features of the present embodiments will be apparent from the accompanying figures, tables and from the detailed description that follows.

DETAILED DESCRIPTION

The present disclosure describes a biological material transfer apparatus (apparatus as will be designated in the following description) to transfer the biological material from one location to another location in an aseptic manner by using sterile disposable tips of fixed size and ball head and re-sterilizing the tips just before they are used.

Figure 1:
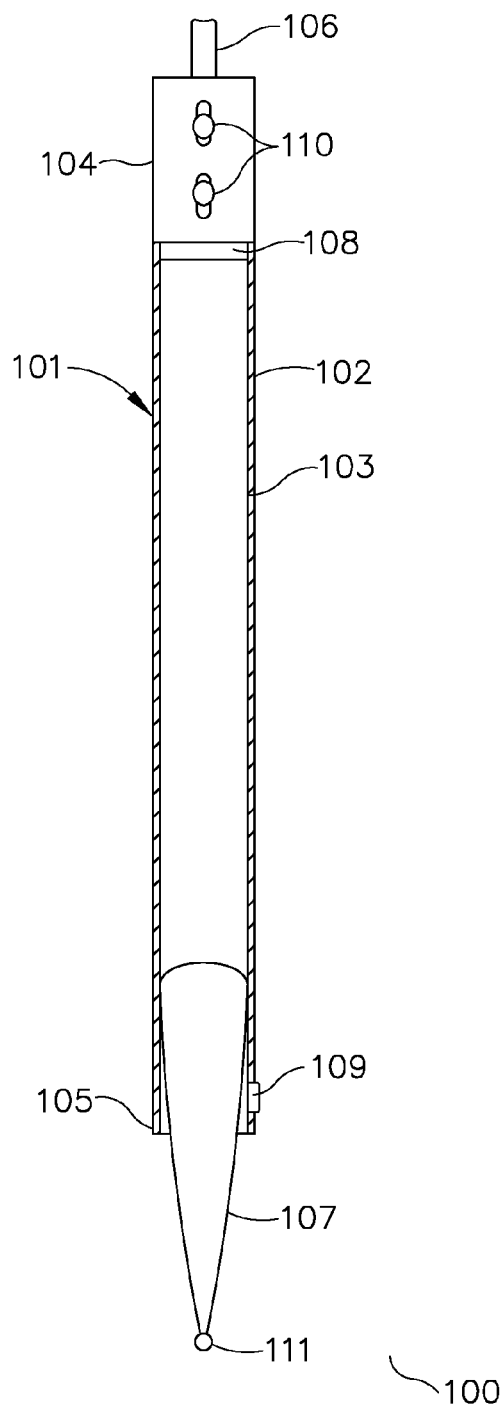
FIG. 1 shows a biological material transfer apparatus for use with a single use tip.

FIG. 1 shows an apparatus 100 as a single use tip apparatus. The apparatus has a barrel shape structure 101 also called the tip chamber 101 with an outer wall 102 and an inner wall 103. The inner wall may be made up of UV protected material such as ceramic, aluminum and synthetic material. The apparatus has an open proximal end 104 and an open distal end 105. At one side of proximal end 104 is an eject button 106 which can be operated by users thumb with ease to lower the disposable tips for use and/or eject the disposable tips 107 from the tip chamber 101. The other side of the open proximal end 104 has a score or push lid 108 that is open to load the disposable tips 107 into the tip chamber 101. The outer wall of tip chamber also has a UV light source 109. There is an ON and OFF switch 110 for UV light source. The disposable tip is lowered from the open distal end with its ball head tip pointing towards the biological material to be transferred.

The UV light source may be located near the open distal end 105 of the tip chamber 101 and thus will aid in re-sterilizing the disposable tips just before it is used. The tip chamber may be sterilized before loading the tips by using the UV light for a specific time and specific wavelength. The tip chamber may also be sterilized after the transfer of biological material is complete to increase the shelf-life of the apparatus and to maintain sterility of the tip chamber.

The UV light source may be present on the outer wall of the tip chamber housed in a UV protected material. Further, one can also place the UV light source at any other location on the outer wall, in between the outer and inner wall or the entire path of tip chamber. The UV light source may be of c-band width so that it can kill mold and mold spores as well as microbial contamination.

The proximal end has a score or push lid which can be opened to load the sterile disposable tips and closed to ensure a one-way entry. The push lid can be easily opened and closed by users thumb. A wire connects the ON and OFF switch button to the UV-C lamp. The apparatus can be either battery operated or electronically operated. The apparatus may be made up of ethanol resistant material such as aluminum, synthetic composite and others.

Figure 2:
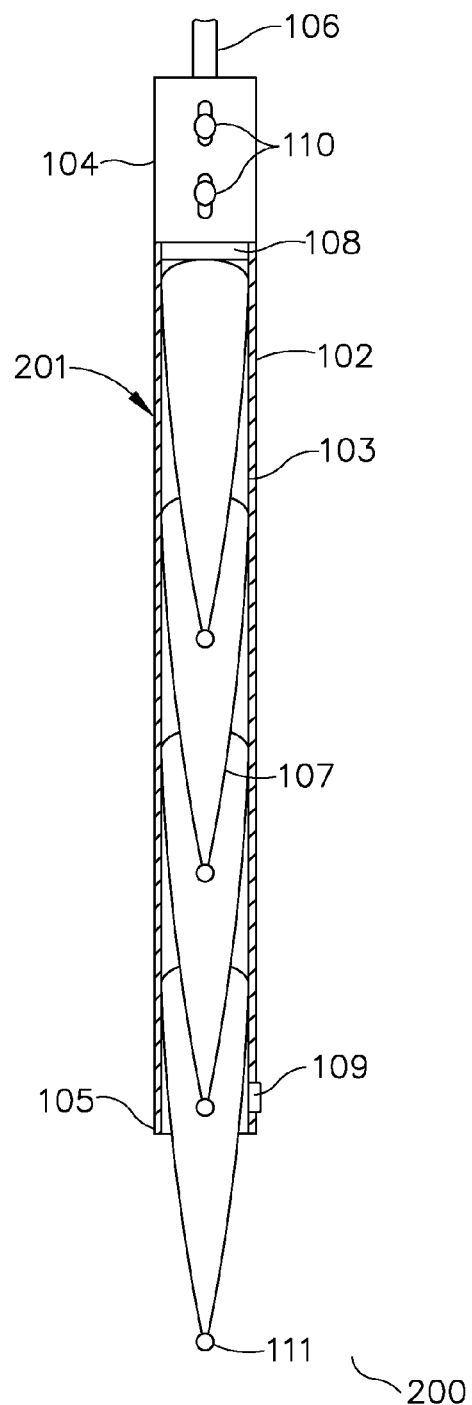
FIG. 2 shows a biological material transfer apparatus for use with multiple use tips.

FIG. 2 shows use of multiple tips with the same apparatus as described in FIG. 1. The disposable tips can be stacked on top of each other. The assembly of multiple use tip is useful so that large scale work can be carried out without any disruption. Further, it also prevents cross-contamination as users do not have to load single tip at one time and also because re-sterilization process is going simultaneously.

Figure 3:
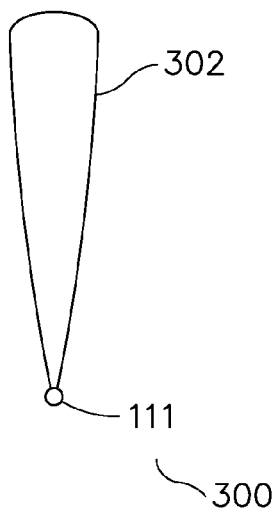
FIG. 3 shows a sterile disposable tip with a fixed length and fixed size of ball head to be used with the presently disclosed apparatus.

FIG. 3 shows the structural details of the disposable tips to be used with the apparatus. The tip has a fixed size shape body and a unique ball shaped head tip which makes it easy to use and easy to pick up the biological material in any form for transfer. The tips may be autoclaved before loading into the tip chamber of the apparatus. This helps in double sterilization of the tips which is very important for sensitive and important transfers of biological materials without cross-contamination. This function enables the tip to be sterilized or re-sterilized just before they are used and come in contact with a biological material. The tips to be used with the apparatus can be pre-sterilized or unsterilized. The pre-sterilized tips can be stored in sterilized packs and directly loaded into the tip chamber. The unsterilized tips can be stored in a box and sterilized to use before loading into the tubular chamber.

The disposable tips may be made available of any particular size and length along with desired ball head size depending on the amount and type of material to be transferred. The ball head tip may be made up of polypropylene or metal so that it is UV resistant and can be easily autoclaved.

Figure 4A:
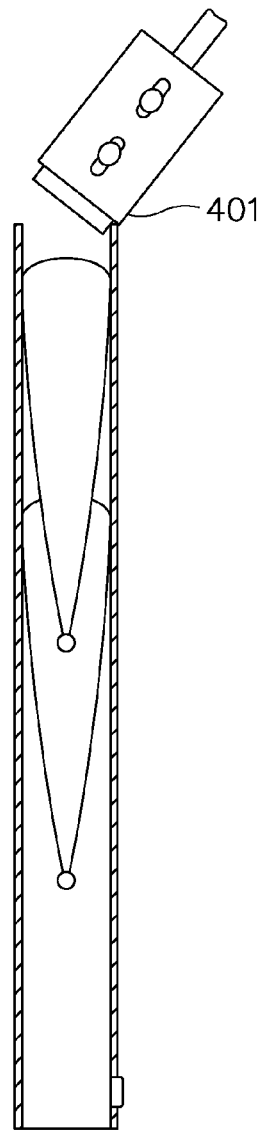
FIG. 4 shows the method of loading the sterile disposable tips into the tip chamber by bringing the score lid to open position (4A) and closing the score lid once the required tips are loaded into the tip chamber (4B).
Figure 4B:
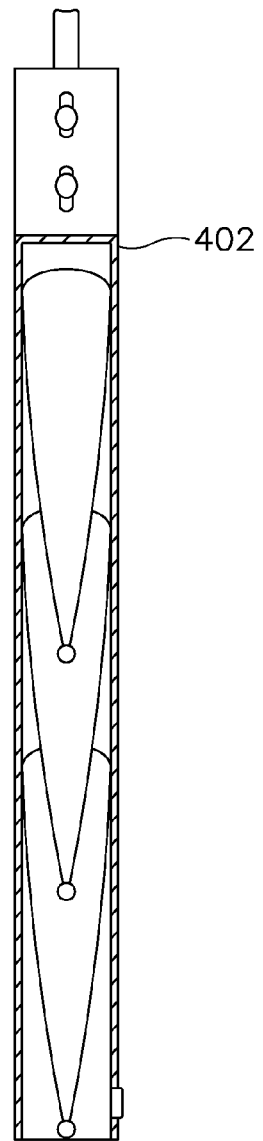

The disposable tips are introduced into the tip chamber from the open proximal end by opening the score or push lid (FIG. 4A) and once the loading of desired number of tips is complete the score lid is brought back to close position (4B).

Figures 5C, 5D:
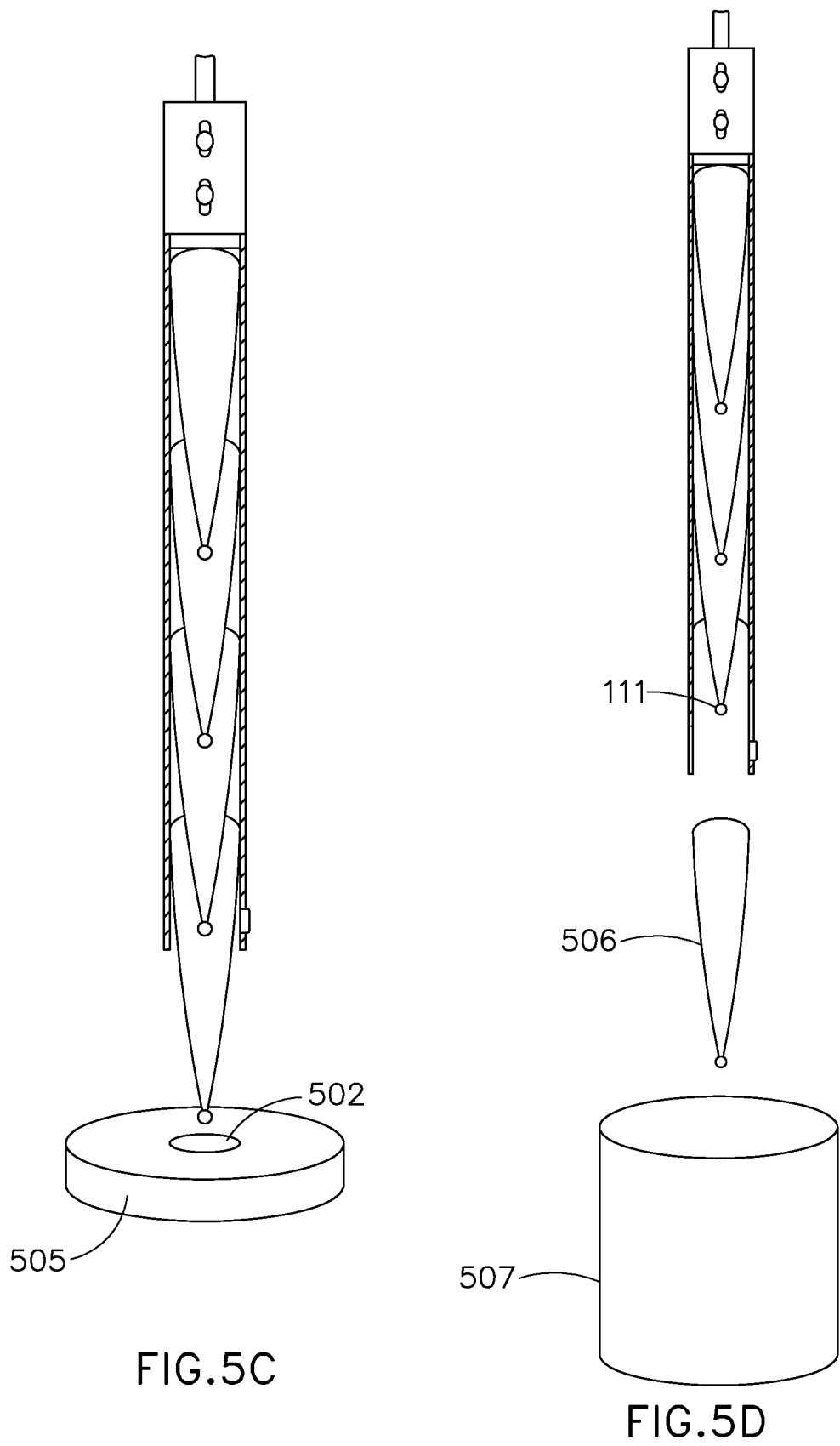
FIG. 5 shows the method of using the apparatus for picking up the biological material by first lowering the ball head of disposable tip (5A), picking up the biological material (5B), transferring the biological material from one location to another location (5C) and ejecting the used tip (5D).

FIG. 5 shows the methodology of using the apparatus 100 or 200 for transferring the biological material from one location to another location. The tip chamber is loaded with a single tip or multiple tips depending on the apparatus to be used and experimental conditions. The tips are pushed down the tip chamber by clicking the eject button manually or electronically. Once the ball head tip reaches the open distal end, it is sterilized by switching ON the UV light source for a pre-determined wavelength and time and then again pushed to get the ball head tip out of the open distal end for the transfer of biological material (5A). This will aid in re-sterilizing the pre-sterilized tips just before they are used. The tip chamber of the apparatus 200 is brought into close proximity of the petri dish 504 (5B). The petri dish contains agar and has several colonies of biological growth for example 502 and 503. The ball head of the sterile tip is lowered up till a convenient distance to pick up the bacterial colonies for example 502. Once the tip head pick up the colony, the tip chamber is pulled upwards to elevate the tip and the material is then transferred to desired petri dish 505 (5C). Once the process of transfer is complete the used tip 506 is discarded by clicking the eject button (5D). the colonies transferred by the method can be bacterial colonies.

Figure 6:
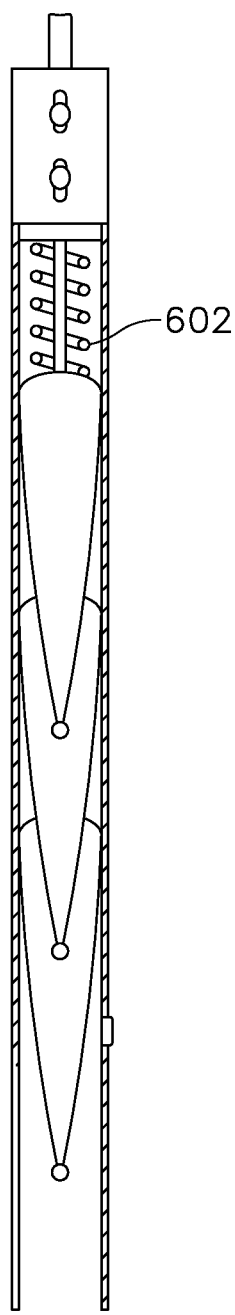
FIG. 6 shows a biological material transfer apparatus having a spring attachment.

Similar methodology is used to transfer the biological material from petri dish, a test tube, a conical flask or other routinely used microbiology laboratory apparatus. FIG. 6 shows a spring like insert 602 to push the tip 111.

Figure 7:
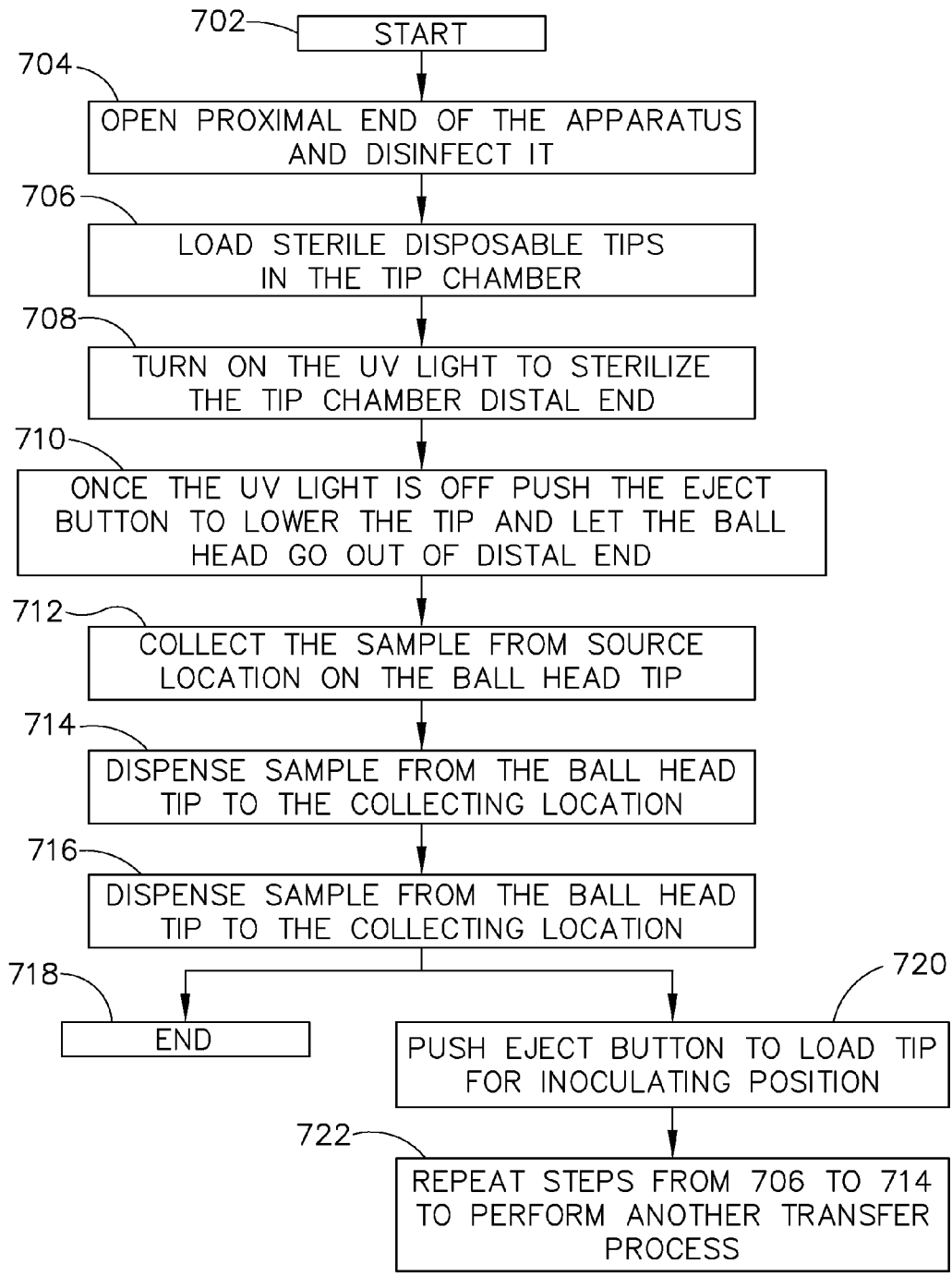
FIG. 7 shows the steps of using the apparatus for transfer of biological material from one location to another location.

FIG. 7 describes the method of using the presently disclosed apparatus as a process flow. A user may sterilize the apparatus before loading the tip. A user may start 702 the process and open the proximal end of the apparatus and disinfect it 704. The user may then turn on the UV light for a predetermined time, for example 2 mins to 10 mins for re-sterilizing the ball head tip present in the distal end of the tip chamber 708. After the predetermined time UV light may switch off automatically and the user push the eject button to lower the tip and let the ball head go out of the distal end for picking the biological material from the petri dish containing agar that is growing a biological material 710. The user then collects the sample from the source location 712. The collected sample is dispensed from the tip to a suitable receiving location 714. The used tip is then discarded in a biological hazard waste container by pushing the eject button 716. The process then either ends 718 or the user may push the eject button again to bring the new tip into the inoculating position 720 and thus repeat the steps from 708 to 716 to transfer the biological sample The apparatus may have either electrical connection for UV light or can be battery operated.

In addition, it will be appreciated that the various integrated container covers and methods of using the integrated container cover disclosed herein may be embodied using means for achieving cost effective material, biodegradable, light weight cheap material and useful apparatus. Accordingly, the specification and drawings are to be regarded in an illustrative rather than a restrictive sense.

INDUSTRIAL APPLICABILITY

The presently disclosed biological material transfer apparatus finds a number of utility in microbiological laboratory procedures as well as in commercial large scale procedures. The apparatus finds utility in transferring the biological material in solid, semi-solid or liquid form with no cross-contaminations as it eliminates the steps of sterilizing the apparatus/tips after every single use. Further, the exposure of UV just before the tip is used helps in carrying out the transfer process in an aseptic condition. The invention can also be used in food industry where packaging of food materials is done under highly aseptic conditions to keep the food contamination to minimum. The size and shape of the tip chamber and ball head tip can be varied which makes it suitable to be used in other material (cell cultures, microbiological cultures, food materials, milk products) transfer techniques under aseptic conditions. The apparatus and methodology disclosed also helps in maintaining health safety of users working in microbiology laboratories or other settings where they come in contact with hazardous biological material. The apparatus and methodology disclosed in the present application also finds utility in biotechnology procedures and experiments.

What is claimed is:

1. A biological material transfer apparatus comprising:
   a barrel shape tip chamber having a double wall and housing a tip therein, wherein the tip is at least one of a single tip and multiple tips, wherein the barrel shaped tip chamber has an inner wall and outer wall;
   the tip having a specific size and ball head, wherein the ball head is used to pick and transfer the biological material from one location to another location;
   a score lid to open and load the tip in the barrel shaped tip chamber and out of the barrel shaped tip chamber for transfer of biological material;
   an ultra violet (UV) light source that is contained within either the inner wall or outer wall of said barrel shaped tip chamber and having a wavelength correlating to UV-C light to sterilize the barrel shaped tip chamber and ball head tip after being switched on for a specific time and having a specific strength.

2. The biological material transfer apparatus of claim 1, wherein the tip has a broad end and a narrow end.

3. The biological material transfer apparatus of claim 2, wherein the narrow end of the tip has a ball head to pick and transfer the biological material from one location to another location.

4. The biological material transfer apparatus of claim 2, wherein the tip is used in at least one of a sterilized manner and unsterilized manner.

5. The biological material transfer apparatus of claim 3, wherein the tip can be sterilized by switching on the UV light before use.

6. The biological material transfer apparatus of claim 1, wherein the tip chamber has an open proximal end and an open distal end.

7. The biological material transfer apparatus of claim 1, wherein the tip chamber is made up of UV protected material such as at least one of a ceramic, aluminum and synthetic material.

8. An aseptic method to perform a biological material transfer, comprising:
   irradiating a barrel shaped tip chamber of the biological material transfer apparatus of claim 1 using the ultra violet light for a specific time and a specific wavelength;
   autoclaving the tip to make a sterile tip and loading the tip on the barrel shaped tip chamber by bring the score lid to an open position;
   lowering the sterile tip into the barrel shaped tip chamber by pushing the eject button until the ball head reaches the distal end;
   re-irradiating the sterile tip by switching on the ultra violet light for the specific time and specific wavelength;
   picking up a biological material from one location and transfer the biological material to another location; and
   discarding the sterile tip after use by pushing the eject button.

9. The aseptic method as in claim 8, wherein the biological material transfer apparatus is a double walled barrel structure having an ultra violet light source built into it.

10. The aseptic method of claim 8, wherein the specific wavelength is UV-C light and the specific time is 2-10 mins.

11. The aseptic method of claim 8, wherein the biological material is a colony of microorganisms grown on an agar plate.

12. The aseptic method of claim 11, wherein the colony of the microorganism is a bacterial colony.

13. The aseptic method as in claim 8, wherein another location is at least a test tube, a petri dish and a conical flask.

14. The aseptic method of claim 8, wherein ball head of the tip is used to pick up the biological material.

15. The aseptic method of claim 8, wherein the ball head has a specific shape and size.

16. The aseptic method of claim 8, wherein the tip is re-irradiated at distal end of barrel shaped tip chamber just before it is used.

* * * * *